US00RE37047E

(19) United States
(12) Reissued Patent
Py

(10) Patent Number: US RE37,047 E
(45) Date of Reissued Patent: Feb. 6, 2001

(54) CARTRIDGE FOR APPLYING MEDICAMENT TO AN EYE FROM A DISPENSER

(76) Inventor: Daniel Py, 40 rue Franklin, St. Germain en Laye (FR), 78100

(21) Appl. No.: 08/567,510

(22) Filed: Dec. 5, 1995

Related U.S. Patent Documents

Reissue of:
(64) Patent No.: 5,267,986
Issued: Dec. 7, 1993
Appl. No.: 07/863,943
Filed: Apr. 6, 1992

(51) Int. Cl.[7] ..... A61M 35/00
(52) U.S. Cl. ..... 604/294; 604/295; 222/214; 222/336
(58) Field of Search ..... 604/294, 295, 604/300, 302; 222/183, 214, 336, 420

(56) References Cited

U.S. PATENT DOCUMENTS

| | | | |
|---|---|---|---|
| Re. 33,801 | 1/1992 | Green . | |
| 2,117,296 | 5/1938 | Cahoon | 221/147 |
| 2,281,051 | 4/1942 | Roger | 221/148 |
| 2,778,360 | 1/1957 | Miskel | 604/87 |
| 3,162,217 | 12/1964 | Poli, Jr. et al. | 141/27 |
| 3,187,960 | 6/1965 | Gorman | 222/321 |
| 3,229,864 | 1/1966 | Roder | 222/321 |
| 3,302,834 | 2/1967 | Alsop | 222/162 |
| 3,411,503 | 11/1968 | Santomieri | 604/87 |
| 3,488,002 | 1/1970 | Mina | 239/327 |
| 3,563,240 | 2/1971 | Silver | 604/87 |
| 3,563,415 * | 2/1971 | Ogle | 222/420 |
| 3,595,439 | 7/1971 | Newby et al. . | |
| 3,684,136 | 8/1972 | Baumann | 604/87 |
| 3,718,139 | 2/1973 | Hanford . | |
| 3,731,853 | 5/1973 | Baumann et al. . | |
| 3,739,947 | 6/1973 | Baumann et al. . | |
| 3,741,439 * | 6/1973 | Vehrs | 222/214 |
| 3,756,390 | 9/1973 | Abbey et al. . | |
| 3,993,064 * | 11/1976 | McCarthy et al. | 604/294 |
| 4,013,370 | 3/1977 | Gingras | 401/175 |
| 4,179,051 | 12/1979 | Thomas | 222/494 |
| 4,220,264 | 9/1980 | Gamadia | 222/207 |
| 4,273,290 | 6/1981 | Quinn | 239/493 |
| 4,296,071 | 10/1981 | Weiss et al. | 864/11 |
| 4,433,797 | 2/1984 | Galia | 222/207 |
| 4,471,890 * | 9/1984 | Dougherty | 604/302 |
| 4,498,904 | 2/1985 | Turner et al. | 604/211 |
| 4,516,969 | 5/1985 | Kinter . | |

*Primary Examiner*—Ronald K. Stright, Jr
*Assistant Examiner*—David J. Cho
(74) *Attorney, Agent, or Firm*—Kenyon & Kenyon

(57) ABSTRACT

A cartridge for actuating a piston-like or accordion-like dispenser-vial for applying medicament to an eye. The cartridge includes a housing for holding the dispenser-vial and a telescoping cylinder for compressing the dispenser-vial in the longitudinal direction to actuate the vial. The cartridge includes a locking mechanism for locking the telescoping cylinder to restrict its movement and a trigger mechanism for releasing the cylinder from the locked position so that a drop is released from the dispenser. The housing includes a finger for engaging the lower eyelid and exposing the conjunctival cul de sac.

15 Claims, 4 Drawing Sheets

U.S. PATENT DOCUMENTS

| | | | | |
|---|---|---|---|---|
| 4,529,511 | | 7/1985 | Breeden et al. | 210/94 |
| 4,531,944 | | 7/1985 | Bechtle | 604/302 |
| 4,623,337 | | 11/1986 | Maurice | 604/298 |
| 4,634,023 | * | 1/1987 | Tanaka et al. | 222/214 |
| 4,639,248 | | 1/1987 | Schweblin | 604/187 |
| 4,648,532 | | 3/1987 | Green | 604/87 |
| 4,673,396 | | 6/1987 | Urbaniak | 604/187 |
| 4,694,977 | | 9/1987 | Graf et al. | 222/259 |
| 4,722,459 | | 2/1988 | Goncalves | 222/135 |
| 4,739,906 | | 4/1988 | LoTurco | 222/494 |
| 4,784,652 | * | 11/1988 | Wilkström | 604/294 |
| 4,792,334 | * | 12/1988 | Py | 604/295 |
| 4,908,024 | | 3/1990 | Py | 604/300 |
| 4,927,062 | | 5/1990 | Walsh | 222/420 |
| 4,930,999 | | 6/1990 | Brunet et al. | 417/552 |
| 4,944,430 | | 7/1990 | Graf et al. | 222/259 |
| 4,946,452 | | 8/1990 | Py | 604/301 |
| 4,950,237 | | 8/1990 | Henault et al. | 604/82 |
| 4,964,544 | | 10/1990 | Hanna et al. | 222/181 |
| 4,981,479 | * | 1/1991 | Py | 604/300 |
| 4,982,875 | * | 1/1991 | Pozzi et al. | 222/420 |
| 5,024,355 | | 6/1991 | Jouillat et al. | 222/162 |
| 5,025,957 | | 6/1991 | Ranalletta et al. | 222/189 |
| 5,038,965 | | 8/1991 | Cater | 222/255 |
| 5,078,691 | | 1/1992 | Hamacher | 604/183 |
| 5,085,651 | | 2/1992 | Py | 604/294 |
| 5,133,702 | * | 7/1992 | Py | 604/300 |
| 5,154,325 | | 10/1992 | Ryder et al. | 222/189 |
| 5,154,702 | * | 10/1992 | Foyil | 222/420 |
| 5,163,583 | * | 11/1992 | Whitworth | 222/420 |
| 5,168,757 | | 12/1992 | Rabenau et al. | 73/714 |
| 5,183,184 | | 2/1993 | Ranalletta et al. | 222/189 |
| 5,190,190 | | 3/1993 | Fudalla | 222/494 |
| 5,207,659 | | 5/1993 | Pennaneac'h et al. | 604/298 |
| 5,238,153 | | 8/1993 | Castillo et al. | 222/189 |
| 5,238,156 | | 8/1993 | Andris | 222/207 |
| 5,255,826 | | 10/1993 | Ranalletta et al. | 222/209 |

* cited by examiner

CARTRIDGE FOR APPLYING MEDICAMENT TO AN EYE FROM A DISPENSER

Matter enclosed in heavy brackets [ ] appears in the original patent but forms no part of this reissue specification; matter printed in italics indicates the additions made by reissue.

*This application is a reissue application of U.S. Pat. No. 5,267,986 issuing from application Ser. No. 07/863,943, filed Apr. 6, 1992.*

BACKGROUND OF THE INVENTION

1. Field of the Invention

The invention relates to a cartridge for applying medicament to an eye from a vial-dispenser of the type which is actuated by compression of the vial between its nozzle and its bottom wall.

2. Description of Related Art

There are various dispensers which are known for applying medicament to an eye. A typical eye-drop container includes a flexible vial storage portion and a nozzle for dispensing drops of medicament into the eye by squeezing the vial between its side walls. Less common, but more precise, are accordion-like or piston-like dispensers which are actuated by squeezing the vial between a bottom wall and the nozzle so as to compress the vial in its longitudinal direction, rather than from its sides. It is these accordion-like or piston-like dispensers with which the cartridge of the present invention is particularly adapted for use. An example of a new and improved piston-like dispenser is the subject of my co-pending U.S. application Ser. No. 07/801,243 which is incorporated herein by reference.

Most people encounter difficulty in applying drops to their eyes. The eye is a very sensitive body part and individuals find it difficult to control reflexive blinking when applying drops thereto. Also, eye drop users often have poor vision. Poor vision makes it difficult to position the tip of the dropper bottle over the eye and frequently causes drops to be incorrectly applied to the nose or cheek. Additionally, elderly people often have difficulty holding a dropper bottle steady or encounter difficulty in squeezing the bottle to apply a proper quantity of the medicament.

Even if the liquid medicament is properly applied to the eye, the medicament's effectiveness is limited. The minimum volume of a drop of liquid medicament which can ordinarily be introduced into contact with an eye at one time is about 30 $\mu$l. Any amount which is greater than about 25 $\mu$l usually spills over the eyelid onto the cheek since this is the maximum volume which the eye can ordinarily handle. When eye drops are applied to the surface of the eyeball, blinking and natural tear flow combine to limit the time to a few minutes that liquid medicament will remain effective.

On the other hand, if medicament is applied to the cul de sac of the conjunctiva, the medicament will remain effective for a longer period of time, maximizing the benefits of applying drops of liquid medicament to the eye. This is because the conjunctiva is an area of low sensitivity and low tear turnover such that blinking and tearing are avoided. However, because of the difficulty encountered in steadying the dropper and accurately positioning it over the conjunctiva, maximizing the effectiveness of the medicament remains elusive.

U.S. Pat. No. 4,543,096 describes and illustrates an apparatus having finger-like projections which are attached to the front of an eye drop bottle to spread the eyelids apart during the eye drop dispensing process. One moveable finger is connected to a lever for both depressing the lever and simultaneously causing the eyelids to spread apart while forcing a drop from the dropper bottle. However, the apparatus described in U.S. Pat. No. 4,543,096 cannot be used with the accordion-like or piston-like dispensers which are actuated by compression in the longitudinal direction rather than from the sides. Furthermore, this apparatus will not properly expose the cul de sac.

Similarly, U.S. Pat. No. 4,531,944 depicts an apparatus for steadying the tip of a dropper over the eye and further includes a sighting hole to distract the eye. However, this apparatus does not have a means to expose the cul de sac nor keep the lower eyelid depressed.

Typical eye-drop dispensers also have the disadvantage that the force which is necessary to actuate the dispenser to emit a drop is not in the same direction as the motion which is necessary to lower the lower eyelid and expose the cul de sac. It would be desirable to have a device which actuates the dispenser with a motion which is in the same direction as that which is necessary to lower the lower eyelid.

SUMMARY OF THE INVENTION

It is an object of the invention to provide a device which can accurately deliver a small drop of medicament to the conjunctival cul de sac of an eye.

It is a further object of the invention to provide such a device which can be used to actuate an accordion-like or piston-like vial-dispenser using minimal force.

It is a further object of the invention to provide such a device wherein the motion used to actuate the dispenser to emit a drop is in the same direction as the motion which is necessary to depress the lower eyelid and expose the conjunctival cul de sac.

It is a further object of the invention to provide a device having these features which has a simple construction and which is easy to manufacture.

The foregoing objects are achieved by the present invention which provides a cartridge which is particularly adapted for actuating an accordion-like or piston-like dispenser-vial. The cartridge includes a generally cylindrical housing which is adapted to receive a dispenser-vial between an anterior wall of the housing and a telescoping cylinder. The anterior wall of the housing has an aperture for allowing the nozzle of the vial to project therefrom. The anterior of the housing is curved with a highly polished and smooth external surface to prevent any corneal injury in the event of accidental contact with the eye.

The back of the housing is open and slidably receives the telescoping inner cylinder. When the inner cylinder is pushed toward the anterior of the housing it forces the dispenser-vial to compress in the longitudinal direction between the anterior wall of the housing and the cylinder. In the case of some dispensers which can be used with the invention, compression causes a drop of liquid medicament to enter the drop cavity of the dispenser thereby "loading" the drop cavity.

The top of the inner surface of the housing is formed with a notch. The front of the telescoping inner cylinder is formed with a rearwardly and outwardly projecting extension which easily slides past an inclined side of the notch as the cylinder is pushed into the housing to load the drop cavity of the vial. However, the opposite side of the notch is angled to prevent the cylinder extension from sliding past the notch in the opposite direction, thereby locking the cylinder so that the vial is in its loaded position.

The housing is formed with a trigger mechanism for unlocking the cylinder. A trigger button is disposed on the top of the housing. Depression of the trigger button forces the extension of the inner cylinder away from the notch allowing the cylinder to move past it. The compressed dispenser-vial forces the inner cylinder rearward. Upon expansion of the dispenser-vial a drop is emitted through the dispenser nozzle.

The bottom of the anterior section of the housing is formed with a soft finger which is adapted to engage the lower eyelid. In order to apply a drop, the inner cylinder is pushed into its locked position to load the dispenser-vial. The nozzle projecting from the cartridge is then positioned over the eyeball with the finger pressing on the lower eyelid to expose the conjunctival cul de sac. When the trigger is depressed the resulting motion of the cartridge will be in the sam direction as the motion which causes the finger to lower the lower eyelid and expose the conjunctival cul de sac as a drop is emitted.

DETAILED DESCRIPTION OF THE INVENTION

Figure 2:
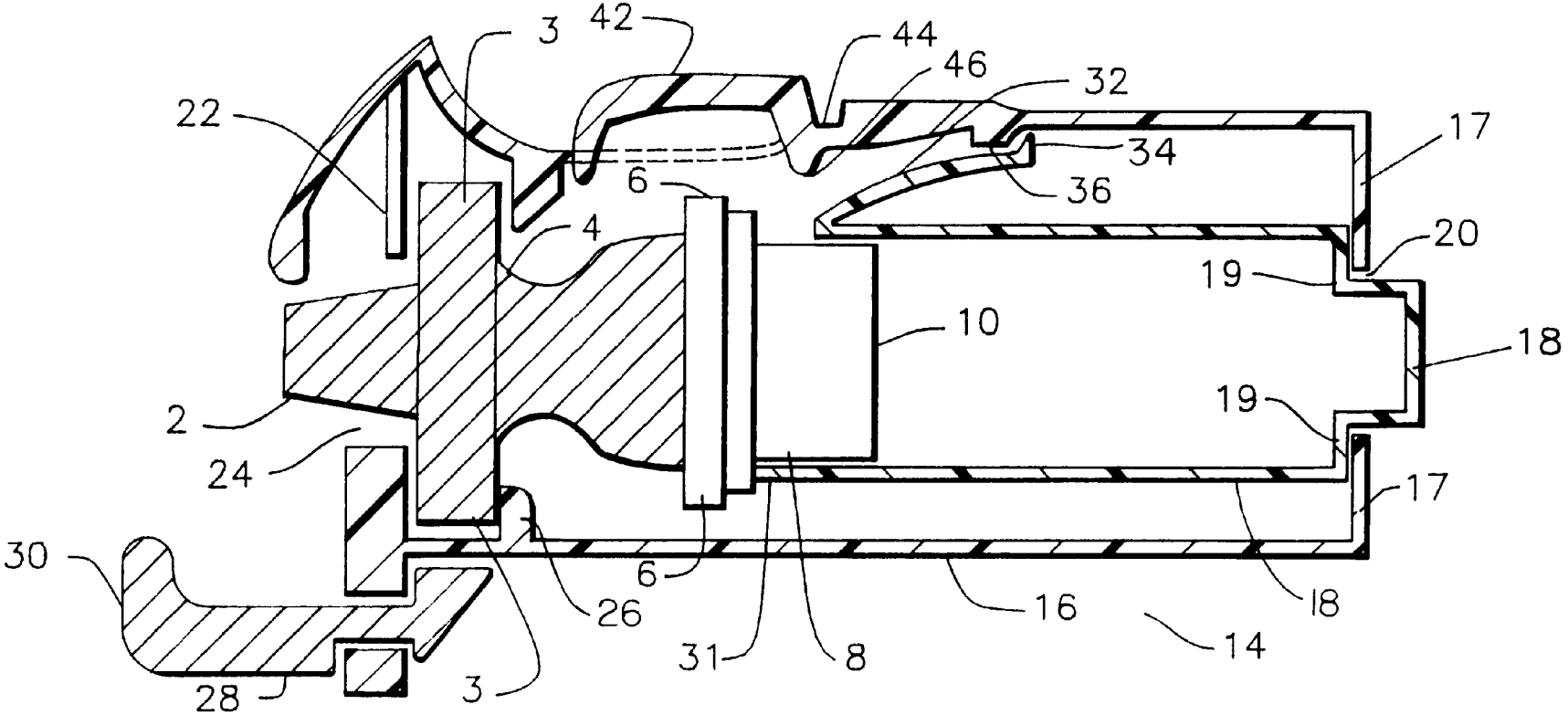
FIG. 2 is a detailed cross-sectional side view of a cartridge in accordance with the invention containing a dispenser-vial.

The cartridge of the invention is specially adapted to work in conjunction with an accordion-like or piston-like dispenser-vial. An example of a new and improved piston-like dispenser which can be used in the cartridge of the invention is the subject of my co-pending application Ser. No. 07/801,243 which is incorporated herein by reference, however, the present invention is not limited to use with this particular dispenser. Parts of a dispenser described in application Ser. No. 07/801,243 which are relevant to an understanding of the present invention are illustrated in FIG. 2 and will now be described briefly to facilitate understanding of the cartridge.

The dispenser-vial includes a nozzle 2, wings 3, a bellows portion 4, wings 6 and a rear vial section 8 containing a storage supply of liquid medicament. The dispenser is compressible in the longitudinal direction between its posterior wall 10 and the anterior nozzle 2. For this purpose, the bellows portion 4 is constructed of a soft flexible plastic material such as the thermoplastic resin sold under the name Kraton from the Shell Company. Resiliency of the dispenser can be provided by the spring quality of the accordion bellows made of Kraton. Kraton has an excellent memory and can be an excellent spring. Alternatively, resiliency may also be provided by a longitudinally disposed spring [(not illustrated)] which urges the dispenser to expand upon compression.

Figure 4:
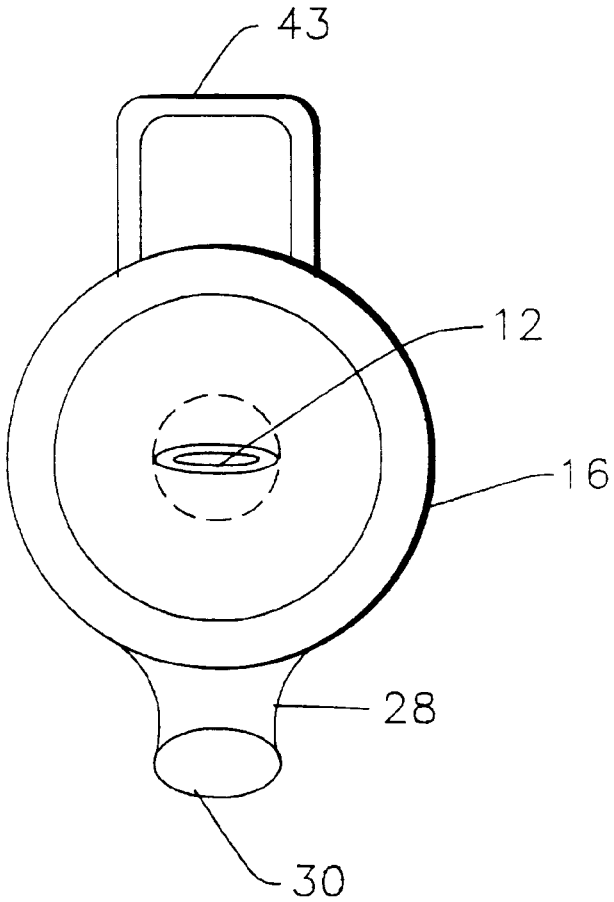
FIG. 4 is a view of the cartridge from the anterior.

The dispenser includes a drop cavity therein [(not illustrated)] which holds a predetermined volume of fluid to be emitted in the form of a drop. Compression of the dispenser in its longitudinal direction creates a drop in pressure in the drop cavity to fill or "load" the drop cavity with liquid where it is stored until it is emitted as a drop from the slit 12 (see FIG. 4) in nozzle 2. This compressed state will be referred to herein as the loaded state. Expansion of the dispenser from the loaded state (caused by the spring urges the fluid in the drop cavity under pressure toward the nozzle 2 from which it is emitted in the form of a drop. It can be seen that the force which is required to actuate this type of dispenser must ordinarily be applied in the direction of the nozzle and hence the eye. [With this background information about the operation of the piston-like dispenser in mind, the cartridge of the invention will now be described.]

*In order to best understand the operation of the cartridge of the invention, the structure and operation of the kind of dispenser-vial which the cartridge of the invention is specifically designed to actuate will now be described in detail with reference to FIGS. 5 ad 6. The dispenser 110 includes an outer body 112, an inner body 114 fitted within the outer body 112, and a piston body 116 coupled to the outer body 112. The outer body 112 and inner body 114 define a nozzle 120 for releasing drops into a user's eye upon movement of the piston body 116 relative to the outer body 112, as indicated by the arrows in FIGS. 5 and 6. The nozzle 120 is the same as the nozzle 20.*

*The outer body 112 defines an outer nozzle portion 122 which receives an inner nozzle portion 124 of the inner body 114. The interface of the outer nozzle portion 122 and the inner nozzle portion 124 defines a seam 125 which is normally closed (i.e., the inner and outer nozzle portions are abutting one another as shown in the drawings), but can be opened by the flow of medicament of sufficient pressure into the seam to release the medicament through the nozzle 120. As with the nozzle 20 described above, the outer body 112 is preferably molded from a relatively flexible plastic material in comparison to the inner body 114. Thus, the outer nozzle portion 122 can be flexed relative to the inner nozzle portion 124 to open the seam 125 to release the medicament through the nozzle 120.*

Figure 5:
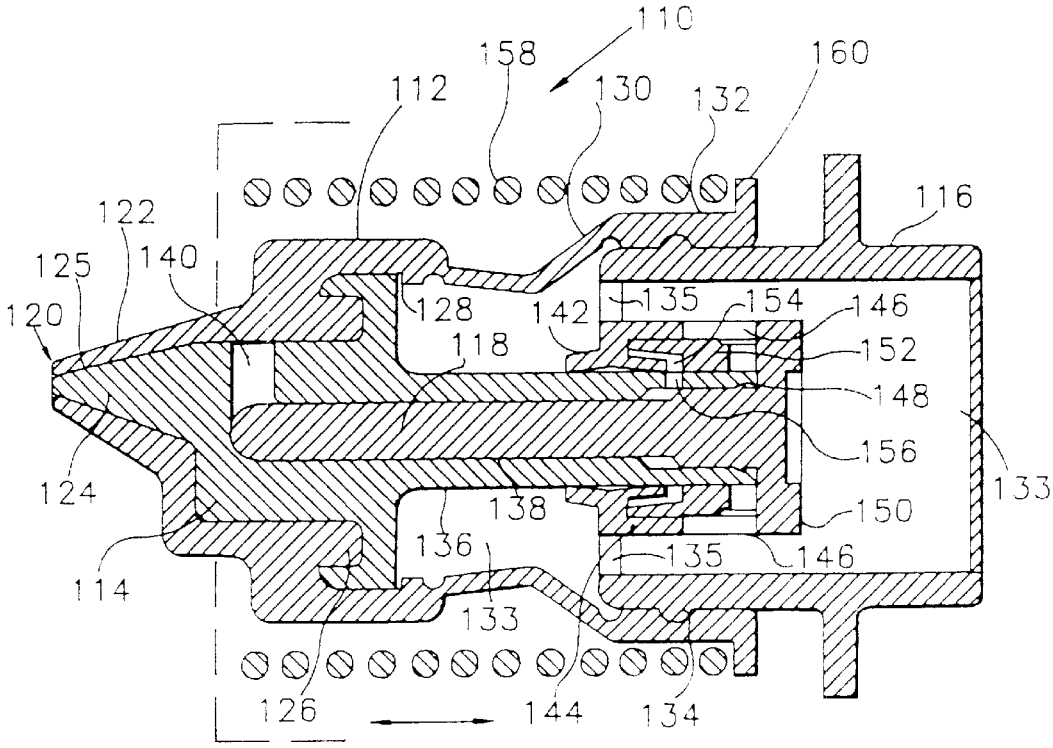
*FIG. 5 is a cross-sectional view of a dispenser-vial which can be housed in and actuated by the cartridge of the invention, wherein the dispenser-vial is illustrated in the expanded position.*
Figure 6:
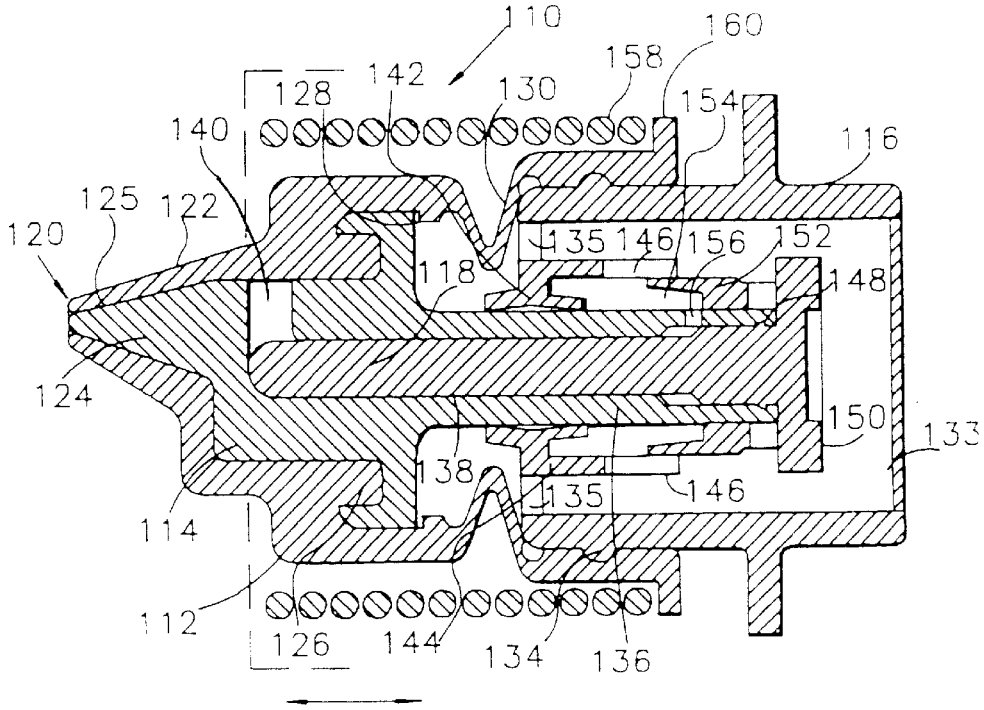
*FIG. 6 is the view of FIG. 5, except the dispenser-vial is illustrated in the compressed position.*

*The outer body 112 includes an annular flange 126 which fits within a corresponding recess in the inner body 114, as shown in FIGS. 5 and 6. The inner body 114, on the other hand, includes an annular lip 128 which retains the inner body 114 within the outer body 112. The inner body 114 is therefore pressed into the outer body 112 and coupled to the outer body by guiding the flange 126 into the corresponding recess and snapping the outer body 114 within the lip 128 of the inner body.*

*The outer body 112 further includes a bellows 130 and a flange 132 coupled to the piston body 116. A medicament chamber 133 is thus defined within the outer body 112 and within the piston body 116, as shown in FIGS. 5 and 6. The piston body 116 includes an aperture 135 to permit the medicament within the chamber 133 to flow between the interior of the outer body 112 and the interior of the piston body 116. The piston body 116 includes a lobe 134 which is snapped into a corresponding recess in the flange 132 to couple the piston body to the outer body 112, as shown in FIGS. 5 and 6. As will be recognized by those skilled in the art, however, the outer body 112 and piston body 116 can equally be molded as an integral body to further prevent any leaks within the apparatus due to changes in the ambient pressure or temperature, for example.*

*The outer end of the piston body 116 is sealed in a manner known to those skilled in the art to retain the medicament*

*within the medicament chamber 133. The other end of the piston body 116 can also be coupled to another container, for example, for pre-packaging the medicament in a manner known to those skilled in the art. The bellows 130 is adapted to flex inwardly to permit the piston body 116 to move relative to the oute body 112 to release medicament stored within the medicament chamber 133 through the nozzle 120.*

*The inner body 114 includes a first substantially cylindrical wall 136 essentially defining a hollow shaft projecting in the axial direction of the dispenser 110 and surrounding a rod member 118, as shown in FIGS. 5 and 6. A first channel 138 is defined between the rod member 118 and the first cylindrical wall 136, and a second channel 140 extends between the first channel 138 and the seam 125.*

*The piston body 116 includes a bushing 142 which receives the first cylindrical wall 136, and thus guides the piston body 116 as it is moved along the first cylindrical wall. As shown in FIGS. 5 and 6, the interior surface of the bushing 142 defines a generally concave profile for engaging the cylindrical wall 136 in a fluid-tight manner, and thus substantially prevents the flow of medicament between the bushing 142 and the cylindrical wall 136 upon moving the piston body 116 to release medicament.*

*The piston body 116 further includes a second cylindrical wall 144 which is substantially concentric with the first cylindrical wall 136, and defines at least two slots 146 coupling the interior of the second cylindrical wall 144 in fluid communication with the medicament chamber 133. As shown in FIGS. 5 and 6, the rod member 118 is coupled to the first cylindrical wall 136 by means of a lobe 148 which snaps into a corresponding recess in the first cylindrical wall. A flange 150 on the end of the rod member 118 rests against the top surfaces of the first cylindrical wall 136 and the second cylindrical wall 144 to prevent the piston body 116 from being moved any further away from the nozzle 120.*

*As shown in FIGS. 5 and 6, a flange member 152 is coupled to the end of the first cylindrical wall 136 and tapers outwardly so that its free end engages the interior surface of the second cylindrical wall 144. The second cylindrical wall 144 and the flange member 152 thus define a drop cavity 154 for holding medicament for release into the eye. The drop cavity 154 is preferably dimensioned to cause less than about 30 microliters of medicament to be released each time the dispenser 110 is actuated. For many medicaments, the drop cavity 154 is preferably dimensioned to release approximately 15 to 20 microliters of medicament each time the apparatus is actuated. This volume of medicament is only exemplary, however, and can be changed as desired by changing the volume of the drop cavity 154, for example. The free end of the flange member 152 is dimensioned so that it engages the interior surface of the second cylindrical wall 144 in order to substantially prevent the flow of medicament between the second cylindrical wall 144 and the flange member 152 upon movement of the piston body 116, as indicated by the arrows in FIGS. 5 and 6. The first cylindrical wall 136 defines an aperture 156 extending between the first channel 138 and the drop cavity 154 to permit the flow of medicament from the drop cavity 154, through the first channel 138 and second channel 140, for release through the nozzle 120 into the eye.*

Figure 3:
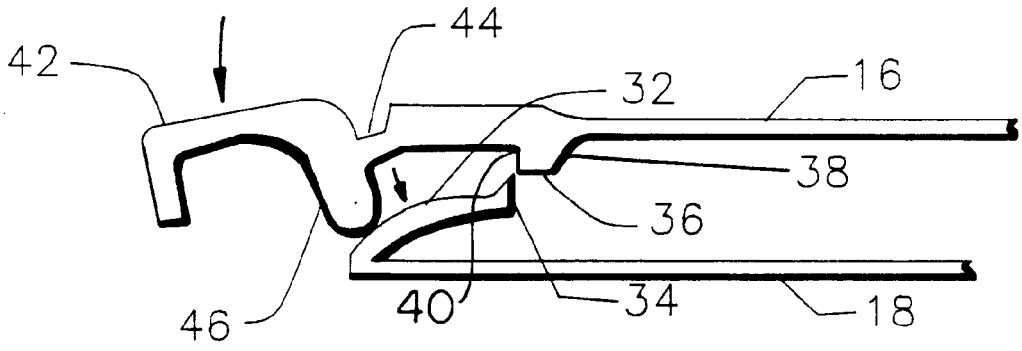
FIG. 3 is an isolated detailed view of the trigger mechanism of the cartridge of the invention.

*In the operation of the dispenser 110, the apparatus is normally oriented in the position shown in FIG. 3 (i.e., the bellows 130 is in a relaxed state). The dispenser 110 is actuated to release medicament through the nozzle 120 by depressing the piston body 116 toward the outer body 112, as shown in FIGS. 6. As a result, the bellows 130 is depressed inwardly and the bushing 142 is moved down toward the nozzle 120, causing a suction to develop within the drop cavity 154, the first channel 138 and the second channel 140. The suction facilitates the flow of medicament from the medicament chamber 133 through the slots 146 to fill the drop cavity 154 and the first and second channels 138 and 140. Once the piston body 116 reaches the end of its downward stroke, as shown in FIG. 6, the piston body is released, thus permitting the coil spring 158 to drive the piston body 116 in the opposite direction away from the nozzle 120.*

*As a result, the bushing 142 slides back along the first cylindrical wall 136 toward the flange member 152. Then, at about the point that the bottom of each slot 146 passes over the end of the flange portion 152, the medicament in the drop cavity 154 is forced by the bushing 142 through the aperture 156 and into the first channel 138. The pressurized medicament flows through the second channel 140, into the seam 125, and out through the tip of the nozzle 120 for release into the eye. The pressure caused by the force of the coil spring 158 driving the bushing 142 is sufficient to cause the medicament to open the seam 125 so that the complete dose of medicament is released into the eye. Then, once the medicament is released, the seam 125 returns to its normally closed position to substantially prevent any medicament that is exposed to air from flowing back into the apparatus. The dispenser 110 is then ready to be actuated again to release another dose of medicament.*

*One advantage of this type of dispenser is that a substantially predetermined volume of medicament can be released into an eye each time the dispenser is actuated. The predetermined volume released can be controlled by controlling the volume of the drop cavity, for example. Another advantage of the dispenser of the present invention is that once a dose of medicament is released, the seam of the nozzle closes, and thus substantially prevents medicament which has been exposed to air or foreign particles from passing through the nozzle and into the apparatus, which can, in some instances, contaminate the remainder of the medicament in the apparatus. This advantage is particularly important when storing multiple-dose quantities of preservative-free formulations of medicament or other substances within the apparatus.*

*Another advantage of the dispenser 110 is that the pumping mechanism, which includes the first cylindrical wall 136 and the actuating member 142, is contained entirely within the medicament chamber 133, and thus further prevents any contamination of the remaining medicament within the apparatus when actuating the pumping mechanism. Another advantage of the dispenser 110 is that the medicament is dispensed upon the release of the piston body 116. In this way, the same quantity of medicament is released each time the apparatus is actuated, because it is the force of the coil spring 158 which causes the medicament to be dispensed from the apparatus. Thus, the dispenser 110 can be used to reliably dispense medicament, regardless of whether a user's hand shakes, or if there are variations in the speed of the downward stroke of the piston body 116.*

*The dispenser 110 may be housed in and actuated by the cartridge of the invention which will now be described. The outer body 112 is seated against a surface of the cartridge which is depicted by phantom lines in FIGS. 5 and 6, in order to maintain the outer body 112 in a stationary position. A coil spring 158 is preferably seated between the surface of the cartridge and an annular lip 160 on the flange 132. The coil spring 158 is provided to drive the piston body 116 to return to its normal position for dispensing medicament.*

Figure 1:
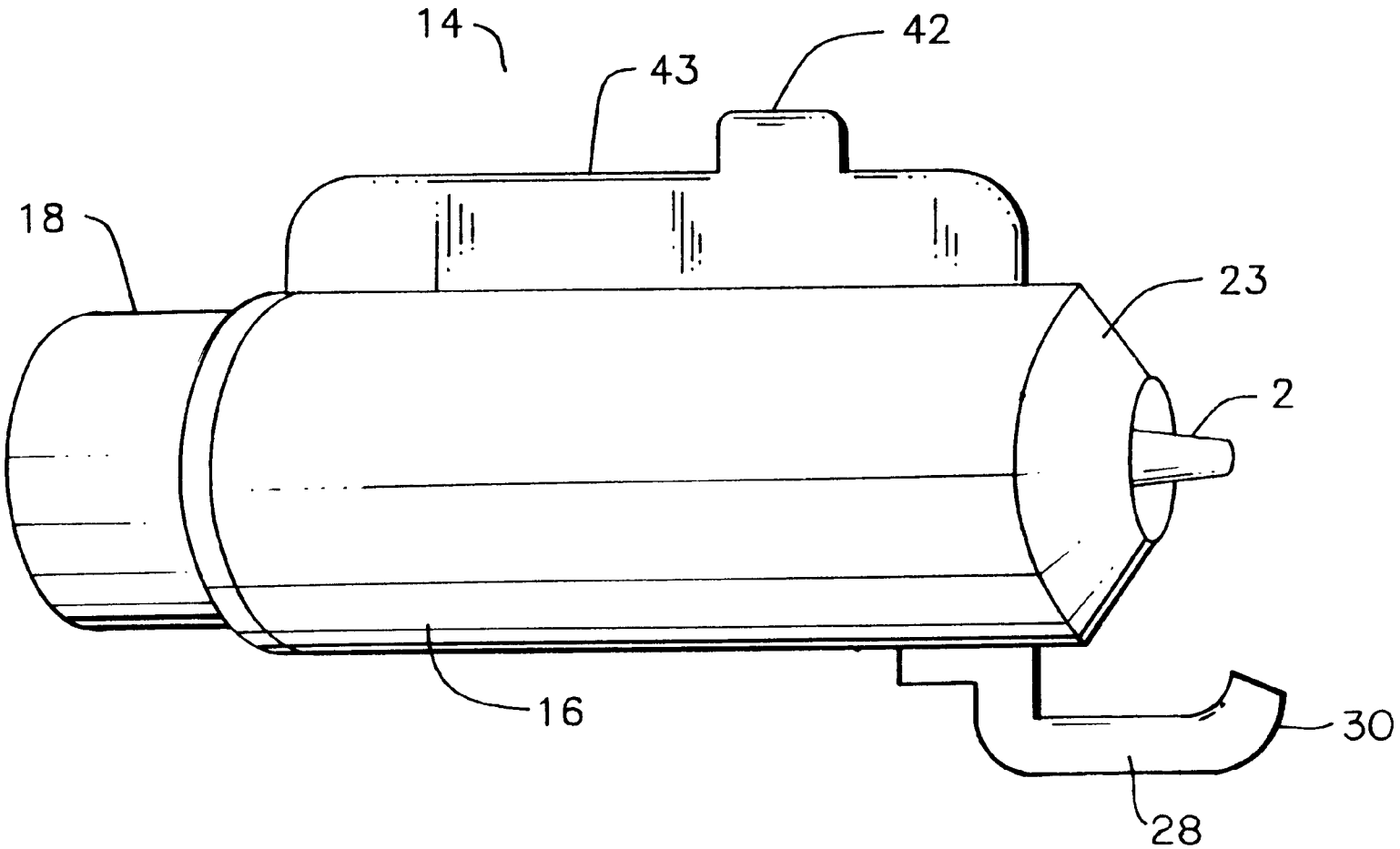
FIG. 1 is a perspective view of a cartridge in accordance with the invention.

Referring to FIGS. 1 and 2, the cartridge which is generally indicated at 14 includes a cylindrical housing 16 which slidably receives an inner cylindrical member 18 through a back open end 20. Preferably, the back of the housing 16 has a wall 17 to fit around the portion of the cylinder 18 which projects outside of the housing. The wall 17 will abut a recessed portion 19 of the inner cylinder 18 to close off the housing to external vapor and moisture.

The front of the housing 1 is substantially closed by an anterior wall 22 which has an aperture 24 centrally located therein allowing for the projection of the nozzle 2 of the dispenser. Preferably, the front of the housing 16 has a smooth arcuate external surface 23 (see FIG. 1) in the event that the cartridge accidentally makes contact with the face. When the dispenser is mounted in the cartridge it sits between the anterior wall 22 and the member 18 as illustrated. The inner surface of housing 16 includes an annular rim 26. Anterior wall 22 and annular rim 26 wedge wing 3 of the dispenser therebetween to prevent displacement of the dispenser within housing 14.

The lower anterior section of housing 16 includes a forwardly projecting finger 28 which extends from the housing 16 beyond the tip of nozzle 2. The finger is upwardly curved to define a smooth surface 30 for engaging the lower eyelid. The finger is preferably coated with a material such as Kraton.

The inner cylinder 18 has a front section 31 which is attached to the vial section 8 of the dispenser. If desired, the inner cylinder 18 may be formed integrally with the storage section 8. The front upper section of the inner cylinder 18 has an outwardly and rearwardly projecting extension 32 which engages and presses against the inner surface of housing 16. The extension 32 is flexible in the direction transverse to the longitudinal axis of the cartridge 14. The tip 34 of the extension 32 has a surface which is positioned and adapted to engage a notch 36 formed on the inside surface of housing 16. The notch 36 is inclined and smooth on its posterior side 38 but is cornered with the housing wall on its anterior side 40. The inner cylinder 18 and extension 32 are positioned in the housing such that the tip 34 of the extension is posterior to the notch 36 when the dispenser is in the non-loaded position.

The cartridge 14 includes a trigger 42. The trigger 42 may be slidably positioned in an opening of an upper housing 43 (see FIG. 1) so as to be capable of inward movement toward the central longitudinal axis of the cartridge. Alternatively, the trigger 42 may be integrally formed with the housing 16 so that it pivots about a thin-walled living hinge section 44 (see FIG. 2). The inner surface of the trigger is formed with a projecting heel 46 whose function will become apparent from the following description of the operation of the cartridge. As illustrated in FIG. 2, preferably the trigger 42 and the point of attachment of the finger 28 to the housing 16 are disposed on opposite upper and lower sides of the housing, respectively, so that they are disposed along the housing 180° apart.

Before positioning the cartridge 14 over the eye, the dispenser-vial in the cartridge is first loaded by pushing the inner cylinder 18 inward thereby compressing the bellows 4 of the dispenser. As the inner cylinder 18 is pushed inward the extension 32 is forced to flex as it slides over notch 36. The tip 34 of extension 32 is able to smoothly slide over the inclined surface 38 of notch 36. Once the tip 34 has passed over the notch 36 the extension 32 will snap back into engagement with the inner surface of housing 16. At this point the dispenser will be in its loaded state as previously defined. In addition, the cartridge 14 is in a locked position because the tip 34 of extension 32 will be unable to move over the cornered surface 40 of notch 36. The cartridge 14 is now ready for positioning over the eye.

As discussed above, a drop of medicament is ideally deposited in the conjunctival cul de sac of the lower eyelid for maximum effectiveness. For this purpose, the engaging surface 30 of finger 28 is gently pressed on the lower eyelid. The cartridge is then moved downward slightly to expose the cul de sac and the cartridge is positioned so that the nozzle 2 will be directed toward the cul de sac. At this point the user would depress the trigger 42.

Referring to FIG. 3, when the trigger 42 is depressed the heel 46 will force the extension 32 downward and the tip 34 will eventually clear the face 40 of notch 36. The spring in the dispenser will force the dispenser and the inner cylinder 18 to expand back to the non-loaded position and at this time a drop of medicament will be released from the slit 12 of nozzle 2 into the eye as discussed above.

It should be appreciated that one advantage of the cartridge of the invention is that the motion which is used to depress the trigger and thereby release a drop is in the same direction as the motion used to lower the eyelid and expose the cul de sac. Therefore, more accurate delivery of the drop is possible. Furthermore, an area of low sensitivity and low tear turn over is specifically targeted by the cartridge which prevents tearing and blinking reflex for better efficacy.

In addition, there is no danger of poking the eyeball with the nozzle 2 since the motion to depress the trigger is not in the direction of the eye and since the finger 28 extends beyond the nozzle. Moreover, when the trigger is depressed the return mechanism of the vial projects the inner cylinder in the direction away from the eye. The cartridge is particularly useful for arthritic patients because the trigger mechanism allows for easy release of a drop.

In the foregoing specification, the invention has been described with reference to specific exemplary embodiments thereof. It will, however, be evident that various modifications and changes may be made thereunto without departing from the broader spirit and scope of the invention as set forth in the appended claims. The specification and drawings are accordingly to be regarded in an illustrative rather than a restrictive sense.

What is claimed is:

1. A cartridge for use with a dispenser for applying medicament to an eye comprising:

a housing having an anterior wall with an aperture therein, the housing having an open back end;

a longitudinally slidable member contained within, said member having a flexible outwardly projecting extension which has a tip engaging an inner surface of the housing;

a notch disposed on the inner surface of the housing having an anterior face and a posterior face which are angled to the housing and which cooperate with the extension tip such that the extension tip can be forced over the posterior face upon sliding the slidable member toward the anterior wall to a locked position where the tip engages the anterior face of the notch, but the tip cannot be forced over the anterior face upon sliding the member toward the back end of the housing from the locked position; and a trigger in the housing having an inner surface for engaging the flexible extension, said trigger being movable to a position where its inner surface forces the flexible extension tip in its locked position in a direction towards the slidable member and away from the inner surface of the housing so that the tip is free to move past the notch upon sliding of the slidable member away from the anterior wall.

2. The cartridge according to claim 1 wherein the housing is cylindrical and wherein the finger is attached along the housing at a point which is about 180° from the location of the trigger.

3. The cartridge according to claim 1 wherein the finger has a surface of a soft thermoplastic material.

4. The cartridge according to claim 1 wherein the inner surface of the trigger has a projecting heel for engaging the flexible extension tip.

5. The cartridge according to claim 1 wherein the posterior face of the notch is a smooth inclined surface and wherein the anterior face of the notch is a flat surface which is normal to the inner surface of the housing.

6. The cartridge according to claim 1 further comprising a finger for engaging an eyelid, the finger projecting from an outer surface of the housing and extending out to a point anterior to the anterior wall.

7. A cartridge in combination with a dispenser for applying medicament to an eye, the dispenser being of the type which is actuated to load a drop of medicament into a cavity therein by compression in its longitudinal direction to a compressed position and which is actuated to emit said drop from a nozzle upon subsequent expansion from said compressed position, the cartridge comprising:

a housing retaining the dispenser therein, the housing having an anterior wall with an aperture therein receiving the nozzle of the dispenser and the housing having an open back end;

a telescoping member, contained within for compressing the dispenser in its longitudinal direction;

a means for locking the telescoping member in a position where the dispenser is in a compressed position; and a trigger means for disengaging the means for locking to allow the dispenser to expand from said compressed position.

8. The cartridge according to claim 7 further comprising a finger for engaging an eyelid, the finger projecting from the housing in an anterior direction to a point anterior to the anterior wall.

*9. A cartridge in combination with a dispenser for applying medicament to an eye, the dispenser comprising: a container holding a volume of fluid; a first dosage cavity forming member and a second dosage cavity forming member, the second member being movable between: a first position, in which the first member and the second member together define a cavity which is in fluid communication with the container; a second position, in which the first member and the second member together define a cavity having a certain predetermined volume and in which the cavity is not in fluid communication with the container; and a third position in which the volume of the cavity is less than the volume of the cavity in the second position and in which the cavity is not in fluid communication with the container; a means for biasing the second dosage cavity forming member to the third position; and a nozzle which is in fluid communication with the cavity, wherein a dosage of fluid in the cavity is forced through the nozzle and out of the apparatus upon movement of the second member from the first position or the second position to the third position under the action of the biasing means, and wherein the second member is selectively movable from the third position back to the first position to draw fluid from the container into the cavity after each dosage of fluid is forced through the nozzle out of the apparatus, the cartridge comprising:*

*a housing which houses the dispenser, the housing having an opening which exposes the nozzle of the dispenser;*

*a pushable member coupled to said housing and being slidable relative to said housing and pushable against a compressible portion of said dispenser, the pushable member being slidable between: a first position wherein the second dosage cavity forming member is in its first position; a second position wherein the second cavity forming member of the dispenser is in its second position; and a third position wherein the second cavity forming member of the dispenser is in its third position, said pushable member being selectively and releasably lockable with respect to the housing in either the first position or the second position so as to releasably lock the second dosage cavity forming member in a corresponding position; and*

*a means for biasing said pushable member and the second dosage cavity forming member toward the third position, said biasing means forcing said pushable member to move from said first or second position to said third position when said pushable member is unlocked relative to said housing in said first or second position.*

*10. The combination according to claim 9 wherein the means for biasing includes a spring.*

*11. The combination according to claim 9 wherein the means for biasing includes a bellows region in the compressible portion of the dispenser.*

*12. The combination according to claim 10 wherein the spring is compressible between a portion of the dispenser and the housing.*

*13. The combination according to claim 9 wherein the means for biasing includes a spring which is biased against one of the dosage cavity forming members of the dispenser.*

*14. A cartridge in combination with a dispenser for applying medicament to an eye, the dispenser being of the type which is actuated to load medicament into a cavity therein by compression of the dispenser and which is actuated to force said medicament from the cavity and out of a nozzle of the dispenser upon subsequent decompression of the dispenser, said cartridge comprising:*

*a housing retaining the dispenser therein;*

*a pushable member coupled to said housing for compressing the dispenser, said pushable member being slidable relative to said housing between a first position in which the dispenser is compressed and a second position in which the dispenser is decompressed, said pushable member being selectively lockable and unlockable in said first position; and*

*a means for biasing said pushable member toward the second position, said biasing means forcing said pushable member to move from said first position to said second position when said pushable member is unlocked in said first position.*

*15. A method of applying a dose of medicament using a cartridge in combination with a dispenser, said dispenser being of the type which is actuated to load medicament from a reservoir therein into a medicament-holding cavity of said medicament from said medicament-holding cavity upon subsequent decompression of said dispenser, said cartridge being of the type which has a movable compressing member for compressing said dispenser and a biasing means operatively coupled to said compressing member, said method comprising:*

*compressing said dispenser by moving said compressing member from a first position to a second position,*

*whereby said medicament is loaded into said medicament-holding cavity;*

*locking said compressing member in said second position relative to said cartridge;*

*unlocking said dispenser in said second position relative to said cartridge; and*

*biasing said compressing member back toward said first position, whereby said dispenser is restored to a decompressed state and said medicament is ejected from said medicament-holding cavity.*

* * * * *